United States Patent [19]

van Reenen

[11] 4,033,352

[45] July 5, 1977

[54] CASTRATING DEVICE

[76] Inventor: Jacob Hellmuth van Reenen, Private Bag 20, P.O. Headlands, Rhodesia

[22] Filed: Sept. 29, 1975

[21] Appl. No.: 617,866

[30] Foreign Application Priority Data

Sept. 30, 1974 Rhodesia .................................. 386

[52] U.S. Cl. .............................................. 128/306
[51] Int. Cl.$^2$ ..................... A61D 1/06; A61B 17/00
[58] Field of Search ................... 30/184, 251, 258; 81/373; 128/306

[56] References Cited

UNITED STATES PATENTS

| | | | |
|---|---|---|---|
| 1,439,225 | 12/1922 | Cashman | 30/251 |
| 1,897,514 | 2/1933 | Hansen | 30/184 |
| 2,040,536 | 5/1936 | Schoonover | 128/306 |
| 2,679,779 | 6/1954 | Spikings | 81/373 |
| 3,159,913 | 12/1964 | Winton | 30/258 X |

*Primary Examiner*—Channing L. Pace
*Attorney, Agent, or Firm*—Berman, Aisenberg & Platt

[57] ABSTRACT

According to the present invention there is provided a castrating device comprising a first arm, a first jaw plate carried by the first arm, a second arm, a pivotal mounting for the second arm, a second jaw plate, means connecting the second jaw plate to the second arm for movement therewith, and means for guiding the second jaw plate so that, when it moves with the second arm, it does so along a rectilinear path towards and away from the first jaw plate, and means for displacing the pivotal mounting of the second arm to enable slackness to be taken up.

The second arm can be pivotally mounted on a tensioning bar which extends longitudinally of the first arm.

10 Claims, 1 Drawing Figure

U.S. Patent
July 5, 1977
4,033,352
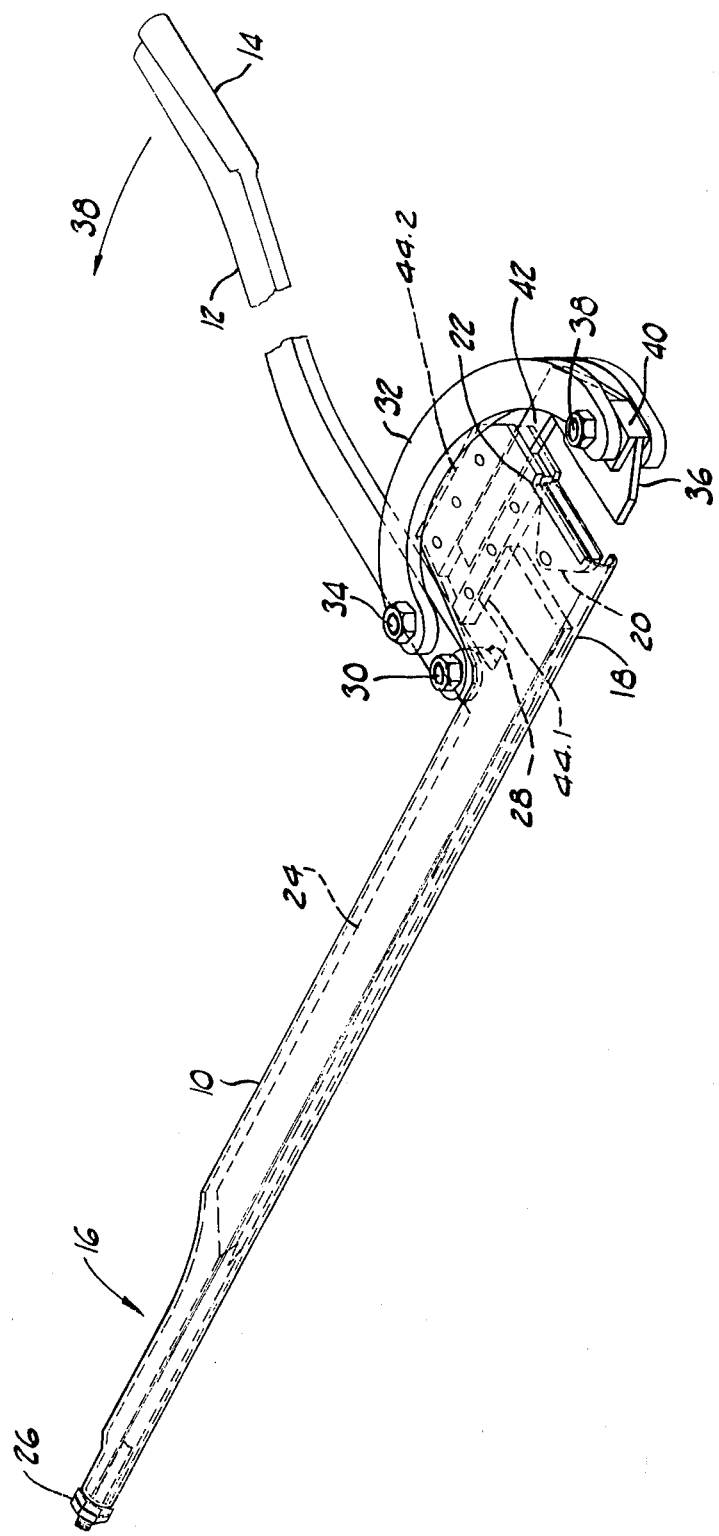

CASTRATING DEVICE

This invention relates to a device for castrating animals.

According to the present invention there is provided a castrating device comprising a first arm, a first jaw plate carried by the first arm, a second arm, a pivotal mounting for the second arm, a second jaw plate, means connecting the second jaw plate to the second arm for movement therewith, and means for guiding the second jaw plate so that, when it moves with the second arm, it does so along a rectilinear path towards and away from the first jaw plate, and means for displacing the pivotal mounting of the second arm to enable slackness to be taken up.

The second arm can be pivotally mounted on a tensioning bar which extends longitudinally of the first arm.

In one form, link means, pivotally connected both to said second arm and to said second jaw plate, form the means for connecting the second arm to the second jaw plate. Said link means can comprise a pair of arcuate links, the links, at one end thereof, sandwiching the second arm between them and, at the other end thereof, sandwiching the second jaw plate between them.

To obtain a large mechanical advantage, it is possible to construct the device so that the pivotal connection between said link means and said second arm is adjacent the pivotal mounting of the second arm and between said pivotal mounting and the free end of the second arm.

In one specific form, said first arm has a gripping portion at one end and a head at the other end, the head being constituted by two spaced plates with said first jaw plate located between them, said guiding means being constituted by guide elements which are also located between said spaced plates, and the second jaw plate having a slider which projects into the gap between said spaced plates and cooperates with said guide elements. Furthermore, it is desirable that the head projects laterally with respect to the elongated portion of the arm of which it forms part, and said first jaw plate projects beyond the edge of the head remote from the junction between the head and said portion of the first arm, said slider being positioned laterally of said first jaw plate and moving in the direction of the length of said portion.

For a better understanding of the present invention, reference will now be made, by way of example, to the accompanying drawing which is a pictorial view of a castrating device.

The device illustrated has two arms 10 and 12, the arm 12 being of solid stock, being shorter than the arm 10 and being formed at its free end 14 so that it can readily be gripped. The arm 10 is constituted by a U-shaped channel of folded metal and one end thereof is tapered inwardly at 16 to form a gripping portion. The other end of the arm 10 is formed with a head 18, there being a metal jaw plate 20 secured within the head between the two spaced plates which constitute the head. The head projects laterally with respect to the elongated portion of the arm 10. The metal plate 20 forms one of the crimping jaws of the device and it will be noted that a channel-shaped guide 22 is formed in that edge of the head 18 from which the plate 20 projects. The edge of the head 18 from which the plate 20 projects, is the edge of the head remote from the junction between the head and the main part of the arm 10.

A tensioning bar 24 is movably secured between the two sides of the U-shaped channel, and extends longitudinally of the arm 10, there being a tensioning device 26 (including a nut and a lock nut) on the threaded free end of the bar 24. The arm 12 is pivotally mounted on an arm 28 by means of a pivot pin 30. The arm 28 forms part of the tensioning bar 24 and extends at right angles to the main part of the tensioning bar 24. It will be noted that the pin 30 is close to the junction between the head 18 and the elongated portion of the arm 10.

A pair of arcuate links 32 is pivotally secured to the arm 12 (adjacent the pivotal mounting of the arm) by means of a pivot pin 34, the links 32 sandwiching the arm 12 between them. At their other ends the links 32 are connected to one another and are pivotally connected to a jaw plate 36 by means of a pivot pin 38. It will be noted that the plate 36 includes a block 40 which acts as a spacer between the links 32. Integral with the plate 36 is a slider 42 and between the flanges of the head 18 there are two elements 44.1 and 44.2 which together define a guideway for the slider 42. Thus the slider 42 is positioned laterally of the jaw plate 20, and both it and the jaw plate 36 are restrained for movement in the direction of the length of said elongated portion of the arm 10. The element 44.1 is abutted by the bar 24 and serves to position the bar 24.

It will be noted that the jaw plate 36 has an operative face which is flat and which is in the form of an elongated rectangle of small width. The operative face of the jaw plate 20 comprises flat, upper and lower, elongated rectangular zones and, between these zones, a recess which, in vertical cross-section, is arcuate in form. The plate 36, in operation, enters the recess and engagement between the jaw plates takes place along the upper and lower edges of the plate 36, that is, along two spaced-apart, parallel lines of contact.

When the arm 12 is moved in the direction of arrow 38, the pivot pin 34 moves along an arc about the pin 30 whereby the jaw plate 36 is moved towards the fixed jaw plate 20. The slider 42 ensures that the jaw plate 36 moves rectilinearly towards and away from the plate 20 and prevents misalignment between the plates. Should, because of rough handling or wear during use, there eventually be slackness in the device, this can be eliminated by loosening the lock nut of the device 26, turning the other nut to tension the bar 24, and re-locking the device 26. This moves the pivot pin 30 and thus compensates for wear.

I claim:

1. In a castrating device which has two jaw plates and two arms, the two arms being pivotally moveable with respect to each other and comprising means for moving the jaw plates rectilinearly so that they may be separated from each other or brought to a closed position in which they are substantially in contact with each other over virtually their entire respective lengths the improvement wherein:
   a. The relative movement of the jaw plates is along a straight path and
   b. wear-compensating means is operatively connected to at least one jaw plate to adjust any pressure between the jaw plates when the latter are in the closed position.

2. A castrating device according to claim 1, comprising a first arm, a first jaw plate carried by the first arm, a second arm, a pivotal mounting for the second arm, a second jaw plate, means connecting the second jaw plate to the second arm for movement therewith, means for guiding the second jaw plate so that, when it moves with the second arm, it does so along a rectilinear path towards and away from the first jaw plate, and means carried by the first arm for displacing the pivotal mounting of the second arm to enable slackness between the jaw plates to be taken up.

3. A castrating device according to claim 2, in which said second arm is pivotally mounted on a tensioning bar which extends longitudinally of the first arm.

4. A device as claimed in claim 2 in which link means pivotally connected both to said second arm and to said second jaw plate form the means for connecting the second arm to the second jaw plate.

5. A device as claimed in claim 4, in which said link means comprises a pair of arcuate links, the links, at one end thereof, sandwiching the second arm between them and, at the other end thereof, sandwiching the second jaw plate between them.

6. A device as claimed in claim 4, in which the pivotal connection between said link means and said second arm is adjacent the pivotal mounting of the second arm and between said pivotal mounting and the free end of the second arm.

7. A device as claimed in claim 2, in which said first arm has a gripping portion at one end and a head at the other end, the head being constituted by two spaced plates with said first jaw plate located between them, said guiding means being constituted by guide elements which are also located between said spaced plates, and the second jaw plate having a slider which projects into the gap between said spaced plates and co-operates with said guide elements.

8. A device as claimed in claim 7, in which said head projects laterally with respect to the elongated portion of the arm of which it forms part, and said first jaw plate projects beyond the edge of the head remote from the junction between the head and said portion of the first arm, said slider being positioned laterally of said first jaw plate and moving in the direction of the length of said portion.

9. A device as claimed in claim 2, in which the jaw plates are shaped so that, when at their closest with no interposed material, they engage one another along two spaced-apart, parallel lines of contact.

10. A castrating device according to claim 2 wherein the relative movement of the jaw plates is along a path which is perpendicular to the jaw plates.

* * * * *